United States Patent [19]

Scrima

[11] Patent Number: 5,268,401
[45] Date of Patent: Dec. 7, 1993

[54] PIPERIDINE-TRIAZINE COMPOUNDS FOR USE AS STABILIZERS FOR ORGANIC MATERIALS

[75] Inventor: Roberto Scrima, Bologna, Italy

[73] Assignee: Ciba-Geigy Corporation, Ardsley, N.Y.

[21] Appl. No.: 690,015

[22] Filed: Apr. 23, 1991

[30] Foreign Application Priority Data

Apr. 30, 1990 [IT] Italy .................. 20175 A/90

[51] Int. Cl.⁵ ............... C08K 5/3492; C07D 295/00; C07D 251/68
[52] U.S. Cl. ....................... 524/100; 524/97; 544/113; 544/198; 544/209; 544/212
[58] Field of Search ............ 544/198, 113, 209, 212; 524/97, 100

[56] References Cited

U.S. PATENT DOCUMENTS

| | | | |
|---|---|---|---|
| 3,729,468 | 4/1973 | Tani et al. | 544/113 |
| 4,108,829 | 8/1978 | Cassandrini et al. | 544/218 |
| 4,321,374 | 3/1982 | Morimura et al. | 544/198 |
| 4,433,145 | 2/1984 | Wiezer et al. | 524/100 |
| 4,491,643 | 1/1985 | Minagawa et al. | 524/96 |
| 4,533,688 | 8/1985 | Yoda et al. | 524/100 |
| 4,547,538 | 10/1985 | Lai et al. | 524/100 |
| 4,740,544 | 4/1988 | Nakahara et al. | 524/100 |
| 4,760,141 | 7/1988 | Nakahara et al. | 544/212 |
| 5,091,450 | 2/1992 | Borzatta et al. | 544/113 |
| 5,102,928 | 4/1992 | Borzatta | 544/113 |

FOREIGN PATENT DOCUMENTS

| | | |
|---|---|---|
| 0022080 | 1/1981 | European Pat. Off. . |
| 0094048 | 11/1983 | European Pat. Off. . |
| 0117229 | 8/1984 | European Pat. Off. . |
| 0148962 | 7/1985 | European Pat. Off. . |
| 0176106 | 4/1986 | European Pat. Off. . |
| 356413 | 2/1990 | European Pat. Off. ............ 544/113 |
| 63-196654 | 8/1988 | Japan . |
| WO8302943 | 9/1983 | PCT Int'l Appl. . |
| 2179940 | 3/1987 | United Kingdom . |

OTHER PUBLICATIONS

Chem. Abst. 106, 6003g (1987).

Derwent 86—248801/38.

Primary Examiner—Kriellion S. Morgan
Attorney, Agent, or Firm—Luther A. R. Hall

[57] ABSTRACT

The present invention relates to novel piperidine-triazine compounds of the general formula (I)

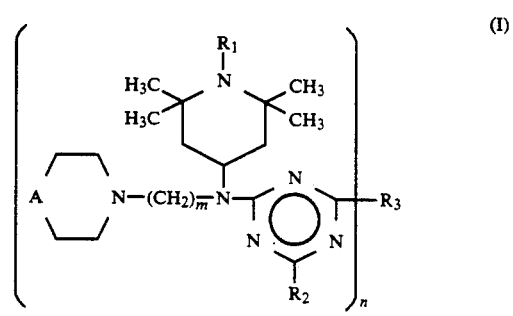

in which $R_1$ is e.g. hydrogen or methyl, A is e.g. —O—, m is e.g. 3, $R_2$ is e.g. a group —$OR_4$ or

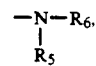

$R_4$ is e.g. $C_1$–$C_4$alkyl, 2,2,6,6-tetramethyl-4-piperidyl or 1,2,2,6,6-pentamethyl-4-piperidyl, $R_5$ and $R_6$ which can be identical or different are e.g. $C_1$–$C_8$alkyl, cyclohexyl, tetrahydrofurfuryl, a group

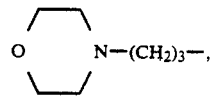

2,2,6,6-tetramethyl-4-piperidyl or 1,2,2,6,6-pentamethyl-4-piperidyl, or $R_5$ can also be hydrogen, or (Abstract continued on next page.)

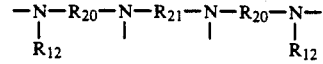

in which $R_{12}$ is e.g. as defined above and $R_{13}$ and $R_{14}$ which can be identical or different are e.g. $C_2$–$C_3$alkylene, and, if n is 4, $R_3$ is e.g. a group

is e.g. 4-morpholinyl, n is 1, 2, 3 or 4 and, if n is 1, $R_3$ is e.g. as defined above for $R_2$ and, if n is 2, $R_3$ is e.g. a group —$E_1$—$R_8$—$E_2$— in which $E_1$ and $E_2$ which can be identical or different are e.g. >N-$R_{12}$, $R_8$ is e.g. $C_2$–$C_6$alkylene, $C_8$–$C_{10}$alkylene interrupted by 2 or 3 oxygen atoms or methylenedicyclohexylene and $R_{12}$ is e.g. hydrogen, methyl, 2,2,6,6-tetramethyl-4-piperidyl or 1,2,2,6,6-pentamethyl-4-piperidyl, and, if n is 3, $R_3$ is e.g. a group

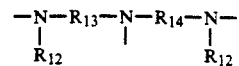

in which $R_{12}$ is e.g. as defined above and $R_{20}$ and $R_{21}$ which can be identical or different are e.g. $C_2$–$C_3$alkylene.

These compounds are effective as light stabilizers, heat stabilizers and oxidation stabilizers for organic materials.

7 Claims, No Drawings

PIPERIDINE-TRIAZINE COMPOUNDS FOR USE AS STABILIZERS FOR ORGANIC MATERIALS

The present invention relates to novel piperidine-triazine compounds, to their use as light stabilizers, heat stabilizers and oxidation stabilizers for organic materials, in particular synthetic polymers, and to organic materials thus stabilized as well as to several intermediates.

It is known that synthetic polymers undergo a photooxidative degradation when they are exposed to sunlight or other sources of ultraviolet light in the presence of oxygen.

When they are used in practice, it is therefore necessary to add suitable light stabilizers to them, such as certain derivatives of benzophenone and benzotriazole, nickel complexes, substituted benzoic acid esters, alkylidenemalonates, cyanoacrylates, aromatic oxamides or sterically hindered amines.

Some triazine compounds containing 2,2,6,6-tetramethylpiperidyl groups and their use as light stabilizers, heat stabilizers and oxidation stabilizers for synthetic polymers have been reported in U.S. Pat. Nos. 4,108,829, 4,321,374, 4,433,145, 4,491,643, 4,533,688 and 4,740,544, in European Laid Open Prints 117,229 and 176,106 and in Japanese Laid Open Prints Sho 61/176,662 and Sho 63/196654.

The present invention relates to the novel compounds of the general formula (I)

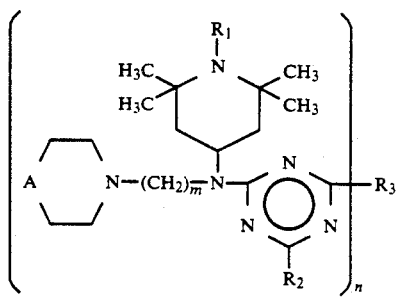
(I)

in which is a direct bond, $-O-$, $-CH_2-$ or $-CH_2CH_2-$, m is an integer from 2 to 6, $R_1$ is hydrogen, $C_1-C_8$alkyl, O, OH, NO, $CH_2CN$, $C_1-C_{18}$alkoxy, $C_5-C_{12}$cycloalkoxy, $C_3-C_6$alkenyl, $C_7-C_9$phenylalkyl unsubstituted or mono-, di- or tri-substituted on the phenyl by $C_1-C_4$alkyl; or $C_1-C_8$acyl, $R_2$ is a group $-OR_4$, $-SR_4$ or

where $R_4$, $R_5$ and $R_6$ which can be identical or different are hydrogen, $C_1-C_{18}$alkyl, $C_5-C_{12}$cycloalkyl unsubstituted or mono-, di- or tri-substituted by $C_1-C_4$alkyl; $C_3-C_{18}$alkenyl, phenyl which is unsubstituted or mono-, di- or tri-substituted by $C_1-C_4$alkyl or $C_1-C_4$alkoxy; $C_7-C_9$phenylalkyl unsubstituted or mono-, di- or tri-substituted on the phenyl by $C_1-C_4$alkyl; $C_2-C_4$alkyl which is substituted in the 2-, 3- or 4-position by $C_1-C_8$alkoxy or by di-$(C_1-C_4$alkyl)-amino; tetrahydrofurfuryl, a group of the formula (II)

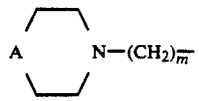
(II)

with A and m being as defined above, or a group of the formula (III)

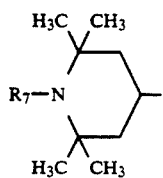
(III)

where $R_7$ is as defined for $R_1$, or

is a 5-membered to 7-membered heterocyclic group, or $R_2$ is any of the groups of the formulae (IVa)-(IVc)

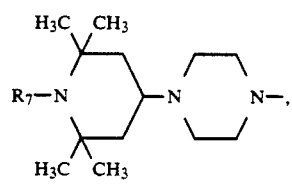
(IVa)

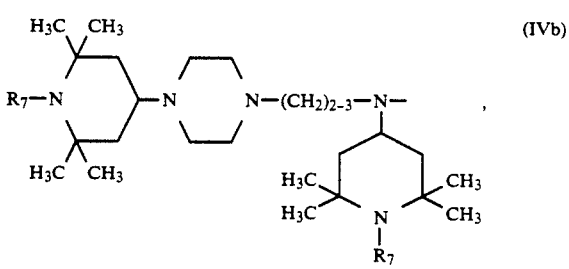
(IVb)

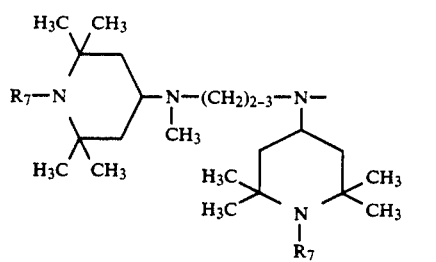
(IVc)

with $R_7$ as defined above, n is 1, 2, 3 or 4, and, if n is 1, $R_3$ is as defined for $R_2$, and, if n is 2, $R_3$ is one of the groups of the formulae (Va)-(Vc)

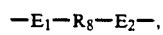
(Va)

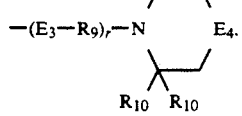
(Vb)

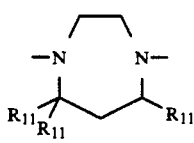 (Vc)

in which $E_1$, $E_2$ and $E_3$ which can be identical or different are —O— or >N—$R_{12}$, $R_8$ is $C_2$-$C_{12}$alkylene, $C_4$-$C_{12}$alkylene interrupted by 1, 2 or 3 oxygen atoms or by 1 or 2>N-$R_{12}$ groups; cyclohexylene, cyclohexylenedimethylene, methylenedicyclohexylene, isopropylidenedicyclohexylene, phenylene, isopropylidenediphenylene or xylylene, $R_9$ is $C_2$-$C_6$alkylene, $E_4$ is >N-($R_9$-$E_3$)$_s$—, >CHO— or >

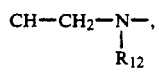

r and s which can be identical or different are zero or 1, $R_{10}$ is hydrogen or, when r is 1 and $E_4$ is >CHO—, can also be methyl, $R_{11}$ is hydrogen or methyl and $R_{12}$ is hydrogen, $C_1$-$C_{18}$alkyl, $C_5$-$C_{12}$cycloalkyl unsubstituted or mono-, di- or tri-substituted by $C_1$-$C_4$alkyl; $C_7$-$C_9$phenylalkyl unsubstituted or mono-, di- or tri-substituted on the phenyl by $C_1$-$C_4$alkyl; or a group of the formula (III), and, if n is 3, $R_3$ is one of the groups of the formulae (VIa)-(VId)

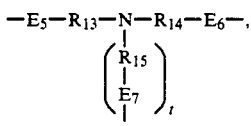 (VIa)

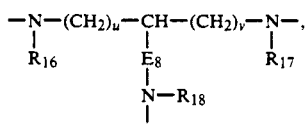 (VIb)

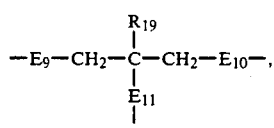 (VIc)

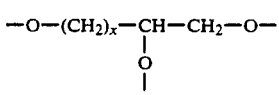 (VId)

in which $E_5$, $E_6$, $E_7$, $E_9$, $E_{10}$ and $E_{11}$ which can be identical or different are as defined above for $E_1$, $E_2$ and $E_3$; and, if $E_9$ and $E_{10}$ are both —O—, $E_{11}$ can also be a —CH$_2$O— group, $R_{13}$, $R_{14}$ and $R_{15}$ which can be identical or different are $C_2$-$C_6$alkylene, t is zero or 1, $R_{16}$, $R_{17}$ and $R_{18}$ which can be identical or different are as defined above for $R_{12}$, $E_8$ is a direct bond or —CH$_2$—, u, v and x which can be identical or different are integers from 2 to 6 and $R_{19}$ is hydrogen or $C_1$-$C_8$alkyl, and, if n is 4, $R_3$ is a group of the formula (VIIa) or (VIIb)

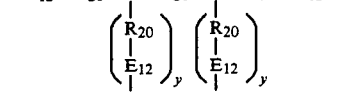 (VIIa)

$R_{22}$(—O—)$_4$ (VIIb)

in which $E_{12}$ is as defined above for $E_1$, $E_2$ and $E_3$; $R_{20}$ and $R_{21}$ which can be identical or different are $C_2$-$C_6$alkylene, y is zero or 1 and $R_{22}$ is $C_4$-$C_{12}$alkanetetrayl.

Examples of alkyl having up to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$-$C_4$alkyl substituted by $C_1$-$C_8$alkoxy, preferably $C_1$-$C_4$alkoxy, especially methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)amino, preferably by dimethylamino or diethylamino, are 2-dimethylaminoethyl, 2-diethylaminomethyl, 3-dimethylaminopropyl, 3-diethylaminopropyl, 3-dibutylaminopropyl and 4-diethylaminobutyl.

Representative examples of $C_1$-$C_{18}$alkoxy $R_1$ and $R_7$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$Alkoxy, in particular heptoxy or octoxy, is preferred.

Examples of the various $C_5$-$C_{12}$cycloalkyl substituents which are unsubstituted or mono-, di- or tri-substituted by $C_1$-$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl which is unsubstituted or substituted by $C_1$-$C_4$alkyl is preferred.

Representative examples of $C_5$-$C_{12}$cycloalkoxy $R_1$ and $R_7$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having up to 18 carbon atoms are allyl, 2-methylallyl, hexenyl, decenyl, undecenyl and oleyl.

Those alkenyl groups are preferred in which the carbon atom in the 1-position is saturated; allyl is particularly preferred.

Examples of substituted phenyl are methylphenyl, dimethylphenyl, trimethylphenyl, t-butylphenyl, di-t-butylphenyl, 3,5-di-t-butyl-4-methylphenyl, methoxyphenyl and ethoxyphenyl.

Examples of the various $C_7$-$C_9$phenylalkyl substituents which are unsubstituted or mono-, di- or tri-substituted on the phenyl by $C_1$-$C_4$alkyl are benzyl, methylbenzyl, dimethylbenzyl, trimethylbenzyl, t-butylbenzyl and 2-phenylethyl. Benzyl is preferred.

Acyl $R_1$ and $R_7$ having up to 8 carbon atoms can be an aliphatic or aromatic group. Representative examples are formyl, acetyl, propionyl, butyryl, pentanoyl, hexanoyl, heptanoyl, octanoyl, benzoyl, acryloyl or crotonoyl. $C_1$-$C_8$Alkanoyl, $C_3$-$C_8$alkenoyl or benzoyl are preferred. Acetyl is particularly preferred.

A 5-membered to 7-membered heterocyclic

can contain a further heteroatom, for example nitrogen or oxygen; representative examples are 1-pyrrolidyl, 1-piperidyl, 4-morpholinyl, 4-methyl-1-piperazinyl and 1-hexahydroazepinyl. 4-Morpholinyl is preferred.

Examples of alkylene having up to 12 carbon atoms are ethylene, propylene, trimethylene, tetramethylene, pentamethylene, 2,2-dimethyltrimethylene, hexamethylene, trimethylhexamethylene, octamethylene, decamethylene and dodecamethylene.

Examples of $C_4$-$C_{12}$alkylene interrupted by 1, 2 or 3 oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl and 3,6,9-trioxaundecane-1,11-diyl.

Representative examples of $C_4$-$C_{12}$alkylene $R_8$ interrupted by 1 or 2 >$NR_{12}$ groups are the groups

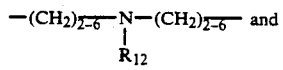

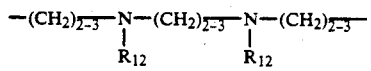

Representative examples of $C_4$-$C_{12}$alkanetetrayl are 1,2,3,4-butanetetrayl and the group

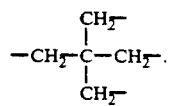

The preferred definitions of $R_1$ and $R_7$ are hydrogen, $C_1$-$C_4$alkyl, OH, $C_6$-$C_{12}$alkoxy, $C_5$-$C_8$cycloalkoxy, allyl, benzyl or acetyl, especially hydrogen or methyl.

Those compounds of the formula (I) are preferred in which A is a direct bond, —O— or —$CH_2$—, m is an integer from 2 to 4, $R_2$ is a group —$OR_4$, —$SR_4$ or

where $R_4$, $R_5$ and $R_6$ which can be identical or different are hydrogen, $C_1$-$C_{14}$alkyl, $C_5$-$C_8$cycloalkyl unsubstituted or mono-, di- or tri-substituted by $C_1$-$C_4$alkyl; $C_3$-$C_{12}$alkenyl, phenyl, benzyl, $C_2$-$C_3$alkyl which is substituted in the 2-or 3-position by $C_1$-$C_4$alkoxy or by di-($C_1$-$C_4$alkyl)-amino; tetrahydrofurfuryl, a group of the formula (II) or a group of the formula (III), or

is 1-pyrrolidyl, 1-piperidyl, 4-morpholinyl, 4-methyl-1-piperazinyl or 1-hexahydroazepinyl, or $R_2$ is one of the groups of the formulae (IVa)-(IVc), n is 1, 2, 3 or 4 and, if n is 1, $R_3$ is as defined for $R_2$, and, if n is 2, $R_3$ is one of the groups of the formulae (Va)-(Vc) in which $E_1$, $E_2$ and $E_3$ which can be identical or different are —O— or >N—$R_{12}$, $R_8$ is $C_2$-$C_{10}$alkylene, $C_4$-$C_{10}$alkylene interrupted by 1, 2 or 3 oxygen atoms or 1 or 2>N—$R_{12}$ groups; cyclohexylenedimethylene, methylenedicyclohexylene, isopropylidenedicyclohexylene, isopropylidenediphenylene or xylylene, $R_9$ is $C_2$-$C_4$alkylene, $E_4$ is >N—($R_9$—$E_3$)$_s$—, >CHO— or >

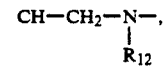

r and s which can be identical or different are zero or 1, $R_{10}$ is hydrogen or, when r is 1 and $E_4$ is >CHO—, can also be methyl, $R_{11}$ is hydrogen or methyl and $R_{12}$ is hydrogen, $C_1$-$C_{12}$alkyl, $C_5$-$C_8$cycloalkyl unsubstituted or mono-, di- or tri-substituted by $C_1$-$C_4$alkyl; benzyl or a group of the formula (III), and, if n is 3, $R_3$ is one of the groups of the formulae (VIa)-(VId) in which $E_5$, $E_6$, $E_7$, $E_9$, $E_{10}$ and $E_{11}$ which can be identical or different are as defined above for $E_1$, $E_2$ and $E_3$; and, if $E_9$ and $E_{10}$ are both —O—, $E_{11}$ can also be a —$CH_2O$— group, $R_{13}$, $R_{14}$ and $R_{15}$ which can be identical or different are $C_2$-$C_6$alkylene, t is zero or 1, $R_{16}$, $R_{17}$ and $R_{18}$ which can be identical or different are as defined above for $R_{12}$, $E_8$ is a direct bond or —$CH_2$—, u, v and x which can be identical or different are integers from 2 to 6 and $R_{19}$ is hydrogen or $C_1$-$C_4$alkyl, and, if n is 4, $R_3$ is a group of the formula (VIIa) or (VIIb) in which $E_{12}$ is as defined above for $E_1$, $E_2$ and $E_3$; $R_{20}$ and $R_{21}$ which can be identical or different are $C_2$-$C_6$alkylene, y is zero or 1 and $R_{22}$ is $C_4$-$C_8$alkanetetrayl.

Those compounds of the formula (I) are particularly preferred in which A is —O— or —$CH_2$—, m is 2 or 3, $R_2$ is a group —$OR_4$, —$SR_4$ or

where $R_4$, $R_5$ and $R_6$ which can be identical or different are hydrogen, $C_1$-$C_{12}$alkyl, cyclohexyl which is unsubstituted or mono-, di- or tri-substituted by $C_1$-$C_4$alkyl; allyl, undecenyl, phenyl, benzyl, $C_2$-$C_3$alkyl which is substituted in the 2- or 3-position by $C_1$-$C_4$alkoxy, by dimethylamino or by diethylamino; tetrahydrofurfuryl, a group of the formula (II) or a group of the formula (III), or

is 4-morpholinyl, or $R_2$ is one of the groups of the formulae (IVa)-(IVc), n is 1, 2, 3 or 4 and, if n is 1, $R_3$ is as defined above for $R_2$, and, if n is 2, $R_3$ is one of the groups of the formulae (Va)-(Vc) in which $E_1$, $E_2$ and $E_3$ which can be identical or different are —O— or >N—$R_{12}$, $R_8$ is $C_2$-$C_8$alkylene, $C_6$-$C_{10}$alkylene interrupted by 2 or 3 oxygen atoms, cyclohexylenedimethylene, methylenedicyclohexylene, isopropylidenedicyclohexylene, isopropylidenediphenylene or xylylene, $R_9$ is $C_2$-$C_3$alkylene, $E_4$ is >N—($R_9$—$E_3$)$_s$— or >CHO—, r and s which can be identical or different are zero or 1, $R_{10}$ is hydrogen or, when r is 1 and $E_4$ is >CHO—, can also be methyl, $R_{11}$ is hydrogen or methyl and $R_{12}$ is hydrogen, $C_1$-$C_8$alkyl, cyclohexyl which is unsubstituted or mono-, di- or tri-substituted by $C_1$-$C_4$alkyl, benzyl or a group of the formula (III), and, if n is 3, $R_3$ is one of the groups of the formulae (VIa)-(VId) in which $E_5$, $E_6$, $E_7$, $E_9$, $E_{10}$ and $E_{11}$ which can be identical or different are as defined above for $E_1$, $E_2$ and $E_3$; and, if $E_9$ and $E_{10}$ are both —O—, $E_{11}$ can also be a —CH$_2$O— group, $R_{13}$, $R_{14}$ and $R_{15}$ which can be identical or different are $C_2$-$C_6$alkylene, t is zero or 1, $R_{16}$, $R_{17}$ and $R_{18}$ which can be identical or different are as defined above for $R_{12}$, $E_8$ is a direct bond or —CH$_2$—, u, v and x which can be identical or different are integers from 2 to 6 and $R_{19}$ is hydrogen, methyl or ethyl, and, if n is 4, $R_3$ is a group of the formula (VIIa) or (VIIb) in which $E_{12}$ is as defined above for $E_1$, $E_2$ and $E_3$; $R_{20}$ and $R_{21}$ which can be identical or different are $C_2$-$C_6$alkylene, y is zero or 1 and $R_{22}$ is $C_4$-$C_6$alkanetetrayl.

Those compounds of the formula (I) are of special interest in which A is —O—, m is 2 or 3, $R_2$ is a group —OR$_4$ or

where $R_4$ is $C_1$-$C_8$alkyl or a group of the formula (III) and $R_5$ and $R_6$, which can be identical or different are $C_1$-$C_8$alkyl, cyclohexyl, benzyl, $C_2$-$C_3$alkyl substituted in the 2- or 3-position by methoxy, by ethoxy, by dimethylamino or by diethylamino; tetrahydrofurfuryl, a group of the formula (II) or a group of the formula (III), or $R_5$ can also be hydrogen, or

is 4-morpholinyl, or $R_2$ is one of the groups of the formulae (IVa)-(IVc), n is 1, 2, 3 or 4 and, if n is 1, $R_3$ is as defined for $R_2$ and, if n is 2, $R_3$ is one of the groups of the formulae (Va)-(Vc) in which $E_1$ and $E_2$ which can be identical or different are —O— or >N—$R_{12}$, $R_8$ is $C_2$-$C_8$alkylene, $C_6$-$C_{10}$alkylene interrupted by 2 or 3 oxygen atoms, cyclohexylenedimethylene or methylenedicyclohexylene, the group (Vb) is

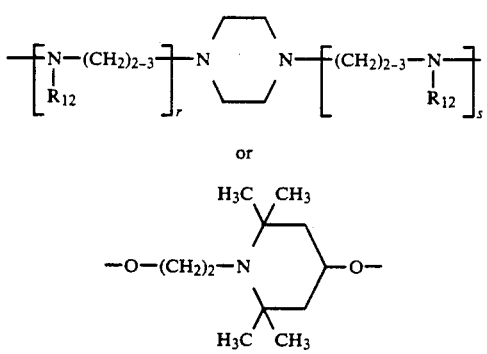

where r and s which can be identical or different are zero or 1, $R_{12}$ is hydrogen, $C_1$-$C_4$alkyl, cyclohexyl or a group of the formula (III) and $R_{11}$ is hydrogen or methyl, and, is n is 3, $R_3$ is a group of the formula (VIa) or (VIb) in which $E_5$, $E_6$ and $E_7$ which can be identical or different are as defined above for $E_1$ and $E_2$; $R_{13}$, $R_{14}$ and $R_{15}$ which can be identical or different are $C_2$-$C_6$alkylene, t is zero or 1, $R_{16}$, $R_{17}$ and $R_{18}$ which can be identical or different are as defined above for $R_{12}$; $E_8$ is a direct bond or —CH$_2$— and u and v which can be identical or different are integers from 3 to 6, and, if n is 4, $R_3$ is a group of the formula (VIIa) in which $E_{12}$ is as defined above for $E_1$ and $E_2$; $R_{20}$ and $R_{21}$ which can be identical or different are $C_2$-$C_3$alkylene and y is zero or 1.

Those compounds of the formula (I) are of particular interest in which $R_1$ is hydrogen or methyl, A is —O—, m is 3, $R_2$ is a group —OR$_4$ or

$R_4$ is $C_1$-$C_4$alkyl, 2,2,6,6-tetramethyl-4-piperidyl or 1,2,2,6,6-pentamethyl-4-piperidyl, $R_5$ and $R_6$ which can be identical or different are $C_1$-$C_8$alkyl, cyclohexyl, tetrahydrofurfuryl, a group

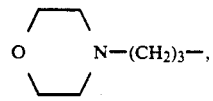

2,2,6,6-tetramethyl-4-piperidyl or 1,2,2,6,6-pentamethyl-4-piperidyl, or $R_5$ can also be hydrogen, or

is 4-morpholinyl, n is 1, 2, 3 or 4 and, if n is 1, $R_3$ is as defined above for $R_2$ and, if n is 2, $R_3$ is a group of the formula (Va) in which $E_1$ and $E_2$ which can be identical or different are >N-$R_{12}$, $R_8$ is $C_2$-$C_6$alkylene, $C_8$-$C_{10}$alkylene interrupted by 2 or 3 oxygen atoms or methylenedicyclohexylene and $R_{12}$ is hydrogen, methyl, 2,2,6,6-tetramethyl-4-piperidyl or 1,2,2,6,6-pentamethyl-4-piperidyl, and, if n is 3, $R_3$ is a group

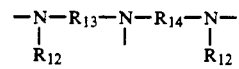

in which $R_{12}$ is as defined above and $R_{13}$ and $R_{14}$ which can be identical or different are $C_2$-$C_3$alkylene, and, if n is 4, $R_3$ is a group

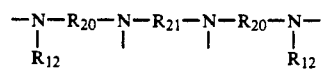

in which $R_{12}$ is as defined above and $R_{20}$ and $R_{21}$ which can be identical or different are $C_2$-$C_3$alkylene.

The compounds of the formula (I) can be prepared by processes known per se, for example by reacting, in any order, cyanuric chloride with the compounds of the formulae (VIIIa)-(VIIIc)

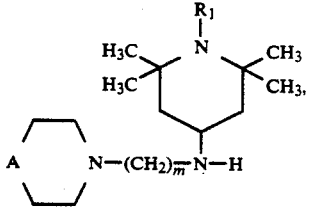

(VIIIa)

$R_2$—H, (VIIIb)

$R_3$—(H)$_n$ (VIIIc)

in the appropriate molar ratios, in particular stoichiometric ratios.

The reactions are preferably carried out in an aromatic hydrocarbon solvent, for example toluene, xylene, or trimethylbenzene, operating at temperatures from e.g. −20° C. to 220° C., preferably from −10° C. to 200° C.

The hydrochloric acid set free in the reaction is preferably neutralized with an inorganic base, for example with sodium or potassium hydroxide or carbonate in a quantity at least equivalent to the acid set free.

If $R_1$ is methyl, the compounds of the formula (I) are preferably prepared by reacting the corresponding compounds, where $R_1$=H, with formaldehyde and formic acid, or with formaldehyde and hydrogen in the presence of a hydrogenation catalyst such as palladium or platinum.

The compounds of the formula (VIIIa) are novel and represent a further embodiment of the instant invention. They can be prepared by reacting e.g. a piperidone of the formula (IX)

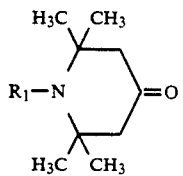

(IX)

with an amine of the formula (X)

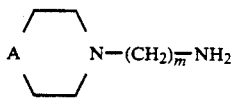

(X)

in the presence of hydrogen and of a hydrogenation catalyst such as platinum, nickel or palladium.

The compounds of the formulae (VIIIb) and (VIIIc), if they are different from those of the formula (VIIIa), are commercially available products or are easily obtainable by known processes.

As mentioned at the outset, the compounds of the formula (I) are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, poly-methylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Copolymers of α-olefins with carbon monoxide, with regular or random alternation.

3b. Hydrocarbon resins (for example $C_5$–$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from copolymers of styrene and other polymers, such as, for example, from a polyacrylate, a diene polymer or an ethylene/propylene/diene terpolymer and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene; styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene; styrene and alkyl acrylates or methacrylates on polybutadiene; styrene and acrylonitrile on ethylene/propylene/diene terpolymers; styrene and acrylonitrile on polyacrylates or polymethacrylates; styrene and acrylonitrile on acrylate/butadiene copolymers, as well as mixtures thereof with the copolymers listed under 5), for instance the mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, such as for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene and polyamides.

14. Polyurethanes which are derived from polyethers, polyesters or polybutadiene with terminal hydroxyl groups on the one hand and aliphatic or aromatic polyisocyanates on the other hand, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensation of m-xylenediamine and adipic acid; polyamides prepared from hexamethylenediamine and isophthalic and/or terephthalic acid and optionally an elastomer as modifier, for example poly-2,4,4-trimethyl-hexamethylene-terephthalamide or poly-m-phenylene-isophthalamide. Further, copolymers of the aforementioned polyamides with polyolefins, olefin copolymers, ionomers or chemically bonded or grafted elastomers; or with polyethers, as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxy carboxylic acids or the corresponding lactones, such as polyethylene terephthalate, polybutylene terephthalate, poly-1,4-dimethylolcyclohexane terephthalate, poly-[2,2-(4-hydroxyphenyl)-propane]terephthalate and polyhydroxybenzoate as well as block copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of the polymers mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratio, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably between 0.05 and 1%.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

In general, the compounds of the formula (I) can be added to the polymeric materials before, during or after the polymerization or crosslinking of the said materials.

The compounds of the formula (I) can be incorporated into the material to be stabilized in a pure form or encapsulated in waxes, oils or polymers.

The materials stabilized with the products of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricylohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl)dithiolterephthalate, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of $\beta$-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.8. Esters of $\beta$-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxamide.

1.9. Esters of $\beta$-(3,5-dicyclohexyl-4hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.10. Amides of $\beta$-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis($\alpha,\alpha$-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of variously substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinnamate, butyl $\alpha$-cyano-$\beta$-methyl-p-methoxycinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone).

2.7. Oxalic acid diamides, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and its mixtures with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis-(1-hydroxy-2,2,6,6,-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

The compounds of the formula (I) can also be used as stabilizers, especially as light stabilizers, for almost all materials known in the art of photographic reproduction and other reproduction techniques as e.g. described in Research Disclosure 1990, 31429 (pages 474 to 480).

Several examples of the preparation and use of the compounds of the formula (I) are reported for more detailed illustration of the present invention; these examples are given solely for illustrative purposes and do not imply any restriction. The intermediate N-(2,2,6,6-tetramethyl-4-piperidyl)-3-morpholinopropylamine as well as the compounds of Examples 2, 4, 8 and 12 are especially preferred.

Preparation of N-(2,2,6,6-tetramethyl-4-piperidyl)-3-morpholinopropylamine 288.4 g (2 mol) of 3-morpholinopropylamine, 310.5 g (2 mol) of 2,2,6,6-tetramethyl-4-piperidone and 300 ml of methanol are introduced into a 2 litre autoclave; 15 g of 5% Pt-on-carbon are added, and hydrogenation is carried out at 60 bar and 60° C. until the absorption of hydrogen ceases (about 15 hours).

After cooling to ambient temperature, the catalyst is removed by filtration, the solvent is removed and the product is purified by distillation: boiling point 93°–95° C./0.13 mbar.

| Analysis for $C_{16}H_{33}N_3O$ | | | |
|---|---|---|---|
| Calculated: | C = 67.80%; | H = 11.73%; | N = 14.82% |
| Found: | C = 67.35%; | H = 11.61%; | N = 14.75% |

EXAMPLE 1

Preparation of the compound of the formula

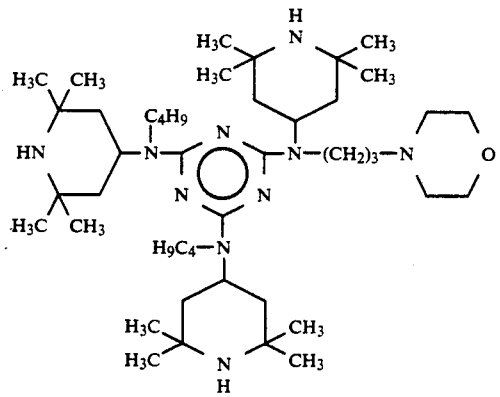

A) Preparation of 2-chloro-4,6-bis[N-(2,2,6,6-tetramethyl-4-piperidyl)-butylamino]-1,3,5-triazine.

85 g (0.4 mol) of 4-butylamino-2,2,6,6-tetramethylpiperidine are slowly added to a solution, cooled to 10° C. of 36.9 g (0.2 mol) of cyanuric chloride in 300 ml of xylene, maintaining the temperature between 10° C. and 20° C.

After the end of the addition, the mixture is stirred for 1 hour at ambient temperature, 16 g (0.4 mol) of sodium hydroxide dissolved in 50 ml of water are added, the mixture is heated for 2 hours at 60° C. and the aqueous layer is then separated off.

B) 56.6 g (0.2 mol) of N-(2,2,6,6-tetramethyl-4-piperidyl)-3-morpholinopropylamine and 16 g (0.4 mol) of ground sodium hydroxide are added to the xylene solution obtained, and the mixture is heated under reflux with removal of the water of reaction and part of the solvent in such a way that an internal temperature of 155° C. is reached after 10 hours, and this temperature is then maintained for a further 10 hours.

After cooling to 70° C., the reaction mixture is diluted with 300 ml of xylene, filtered and evaporated under reduced pressure. The residue is crystallized from acetonitrile.

The product obtained melts at 77°-80° C.

| Analysis for C$_{45}$H$_{86}$N$_{10}$O | | | |
|---|---|---|---|
| Calculated: | C = 69.01%; | H = 11.07%; | N = 17.88% |
| Found: | C = 68.34%; | H = 10.99%; | N = 17.72% |

EXAMPLE 2

Preparation of the compound of the formula

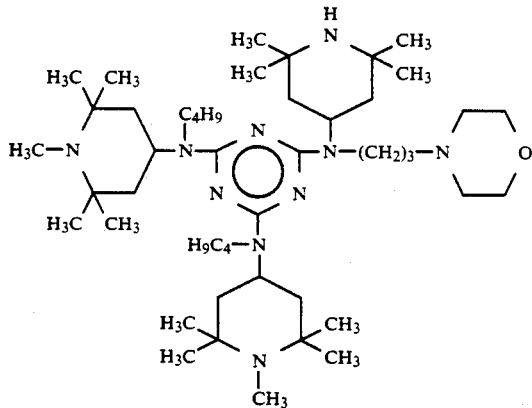

A) Preparation of 2-chloro-4,6-bis-[N-(1,2,2,6,6-pentamethyl-4-piperidyl)-butylamino]-1,3,5-triazine.

A xylene solution of 2-chloro-4,6-bis-[N-(2,2,6,6-tetramethyl-4-piperidyl)-butylamino]-1,3,5-triazine is prepared as described in Example 1A, using the same quantities of reagents.

A mixture containing 20.2 g (0.44 mol) of formic acid and 46 g (0.46 mol) of a methanol-free 30% aqueous solution of formaldehyde is added in the course of 3 hours to the above solution, heated to 110° C., with simultaneous removal of the water added and the water of reaction.

The reaction mixture is then cooled to 70° C., a solution of 3 g of sodium hydroxide in 20 ml of water is added and the mixture is stirred for 30 minutes.

After separating off the aqueous phase, the organic layer is washed with water and evaporated under reduced pressure. The residue is crystallized from acetone. The product obtained melts at 131°-133° C.

Cl = 6.30% (calculated for C$_{31}$H$_{58}$ClN$_7$ = 6.28%).

B) A mixture of 56.4 g (0.1 mol) of 2-chloro-4,6-bis-[N-(1,2,2,6,6,-pentamethyl-4-piperidyl)-butylamino]-1,3,5-triazine, 28.3 g (0.1 mol) of N-(2,2,6,6-tetramethyl-4-piperidyl)-3-morpholinopropylamine, 8 g (0.2 mol) of ground sodium hydroxide and 200 ml of mesitylene is heated under reflux with removal of the water of reaction and part of the solvent in such a way that an internal temperature of 175° C. is reached after 10 hours, and heating is continued at this temperature for a further 10 hours.

After cooling to 70° C., the reaction mixture is diluted with 200 ml of mesitylene, filtered and evaporated under reduced pressure. The residue is crystallized from hexane.

The product obtained melts at 87°-90° C.

| Analysis for C$_{47}$H$_{90}$N$_{10}$O | | | |
|---|---|---|---|
| Calculated: | C = 69.58%; | H = 11.18%; | N = 17.26% |
| Found: | C = 69.26%; | H = 11.10%; | N = 17.23% |

EXAMPLE 3

Preparation of the compound of the formula

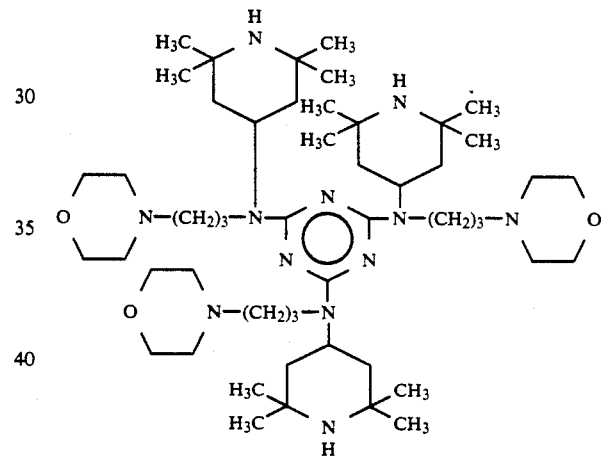

85 g (0.3 mol) of N-(2,2,6,6-tetramethyl-4-piperidyl)-3-morpholinopropylamine, dissolved in 80 ml of mesitylene, are added slowly to a solution of 18.4 g (0.1 mol) of cyanuric chloride in 200 ml of mesitylene, maintaining the temperature between 20° and 50° C.

The mixture is stirred for 1 hour at room temperature, 16 g (0.4 mol) of ground sodium hydroxide are added and the mixture is heated under reflux with removal of the water of reaction and part of the solvent in such a way that an internal temperature of 190° C. is reached after 10 hours, and this temperature is maintained for a further 10 hours.

After cooling to 70° C., the reaction mixture is diluted with 200 ml of mesitylene, filtered and evaporated under reduced pressure.

The residue is crystallized from hexane.

The product obtained melts at 167°-170° C.

| Analysis for C$_{51}$H$_{96}$N$_{12}$O$_3$ | | | |
|---|---|---|---|
| Calculated: | C = 66.19%; | H = 10.46%; | N = 18.16% |
| Found: | C = 66.08%; | H = 10.55%; | N = 17.89% |

EXAMPLE 4

Preparation of the compound of the formula

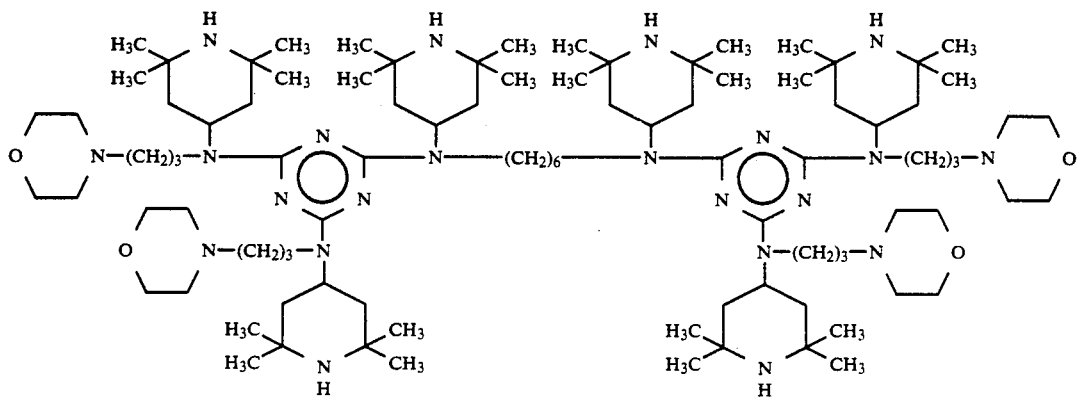

A) Preparation of 2-chloro-4,6-bis-[N-(3-morpholino-propyl)-N-(2,2,6,6-tetramethyl-4-piperidyl)-amino]-1,3,5-triazine.

A solution of 138.4 g (0.75 mol) of cyanuric chloride in 1200 ml of xylene is added slowly to a solution of 425.2 g (1.5 mol) of N-(2,2,6,6-tetramethyl-4-piperidyl)-3-morpholinopropylamine in 800 ml of xylene, maintaining the temperature between 20° and 50° C.

The mixture is then stirred for 1 hour at ambient temperature, 60 g (1.5 mol) of sodium hydroxide dissolved in 170 ml of water are added and the mixture is heated for 2 hours at 100° C. After cooling to ambient temperature, the aqueous phase is separated off, and the organic layer is dehydrated over $Na_2SO_4$, filtered and evaporated under reduced pressure. The residue is crystallized from ethyl acetate.

The product obtained melts at 68°–71° C.

Cl = 5.25% (calculated for $C_{35}H_{64}ClN_9O_2$ = 5.23%).

B) 67.8 g (0.1 mol) of 2-chloro-4,6-bis-[N-(3-morpholinopropyl)-N-(2,2,6,6-tetramethyl-4-piperidyl)-amino]-1,3,5-triazine, 19.7 g (0.05 mol) of N,N'-bis-(2,2,6,6-tetramethyl-4-piperidyl)-1,6-hexanediamine and 8 g (0.2 mol) of ground sodium hydroxide in 200 ml of mesitylene are heated under reflux with removal of the water of reaction and part of the solvent in such a way that an internal temperature of 190° C. is reached after 10 hours, and heating is continued at this temperature for a further 10 hours.

After cooling to 70° C., the reaction mixture is diluted with 200 ml of mesitylene, filtered and evaporated under reduced pressure. The residue is crystallized from acetone.

The product obtained melts at 212°–215° C.

| Analysis for $C_{94}H_{176}N_{22}O_4$ | | | |
|---|---|---|---|
| Calculated: | C = 67.26%; | H = 10.57%; | N = 18.36% |
| Found: | C = 67.02%; | H = 10.45%; | N = 18.14% |

EXAMPLES 5-6

Following the procedure described in Example 4 and using the respective reagents in the appropriate molar ratios, the following compounds of the formula

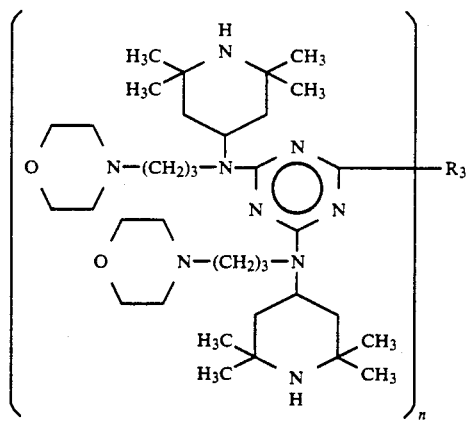

are prepared.

| Example | n | $R_3$ | Melting point (°C.) |
|---|---|---|---|
| 5 | 3 | —HN$\pmb{(}$CH$_2)_3$N$\pmb{(}$CH$_2)_3$NH— | 101–104 |
| 6 | 4 | —HN$\pmb{(}$CH$_2)_3$N$\pmb{(}$CH$_2)_2$N$\pmb{(}$CH$_2)_3$NH— | 103–107 |

EXAMPLE 7

Preparation of the compound of the formula

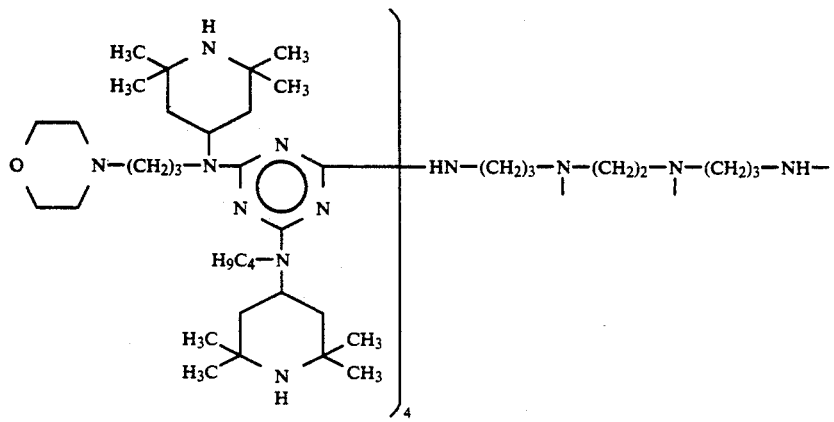

42.5 g (0.2 mol) of 4-butylamino-2,2,6,6-tetramethyl-piperidine are added slowly to a solution, cooled to 0° C., of 36.9 g (0.2 mol) of cyanuric chloride in 300 ml of xylene, without exceeding 10° C. A solution of 8 g (0.2 mol) of sodium hydroxide in 30 ml of water is then added slowly, maintaining the temperature at 10° C. The mixture is stirred for 1 hour at 10°-20° C., and 56.7 g (0.2 mol) of N-(2,2,6,6-tetramethyl-4-piperidyl)-3-morpholinopropylamine are then added and the mixture is heated at 50° C. for 4 hours.

After cooling to ambient temperature, a solution of 8 g (0.2 mol) of sodium hydroxide in 30 ml of water is added and the mixture is stirred for 2 hours at the same temperature.

The aqueous phase is separated off, 8.7 g (0.05 mol) of N,N'-bis-(3-aminopropyl)-1,2-ethanediamine and 16 g (0.4 mol) of ground sodium hydroxide are added and the mixture is heated under reflux with removal of the water of reaction and part of the solvent in such a way that an internal temperature of 160° C. is reached after 10 hours, and heating at this temperature is then continued for 13 hours.

After cooling to 70° C., the reaction mixture is diluted with 300 ml of xylene, filtered and evaporated under reduced pressure.

The product obtained melts at 111°-115° C.

Analysis for $C_{136}H_{254}N_{36}O_4$

| | | | |
|---|---|---|---|
| Calculated: | C = 66.46%; | H = 10.42%; | N = 20.52% |
| Found: | C = 65.50%; | H = 10.28%; | N = 20.28% |

EXAMPLE 8

Preparation of the compound of the formula

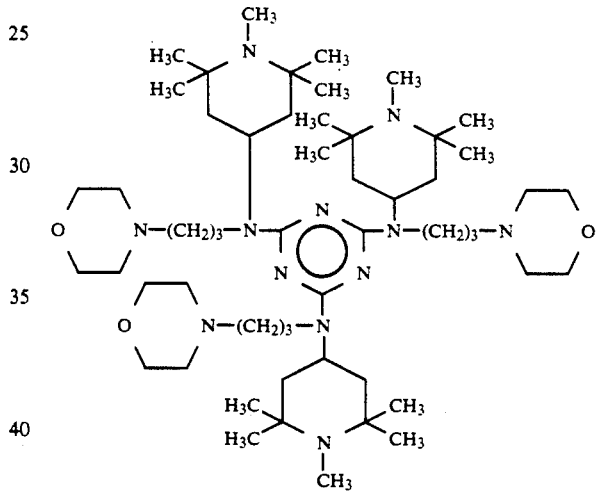

A mixture containing 7.6 g (0.165 mol) of formic acid and 17 g (0.17 mol) of a methanol-free 30% aqueous formaldehyde solution is added in the course of 3 hours to a solution, heated to 110° C., of 46.3 g (0.05 mol) of the compound prepared according to Example 3 in 150 ml of xylene, with simultaneous removal of the water added and that of reaction.

The reaction mixture is then cooled to 70° C., a solution of 8 g of sodium hydroxide in 50 ml of water is added, and the mixture is stirred for 30 minutes. After the aqueous phase has been separated off, the organic layer is washed with water, dried over $Na_2SO_4$ and evaporated under reduced pressure.

The product obtained melts at 94°-97° C.

Analysis for $C_{54}H_{102}N_{12}O_3$

| | | | |
|---|---|---|---|
| Calculated: | C = 67.04%; | H = 10.63%; | N = 17.37% |
| Found: | C = 66.31%; | H = 10.41%; | N = 17.29% |

EXAMPLES 9-11

Following the procedure described in Example 8 and using the compounds from Examples 4, 5 and 6, the following compounds of the formula

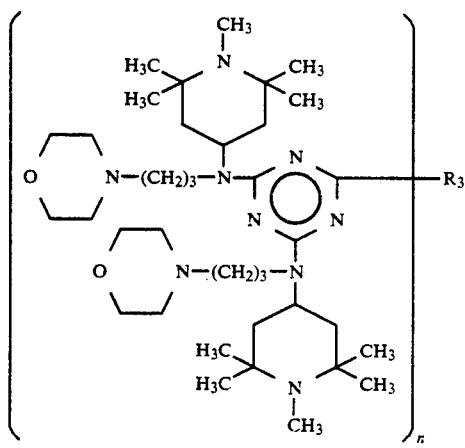

are prepared.

| Example | n | R₃ | Melting point (°C.) |
|---|---|---|---|
| 9 | 2 | (structure shown) | 134–140 |
| 10 | 3 | —HN$\pm$CH₂$\frac{1}{3}$N$\pm$CH₂$\frac{1}{3}$NH— | 114–120 |
| 11 | 4 | —HN$\pm$CH₂$\frac{1}{3}$N$\pm$CH₂$\frac{1}{3}$N$\pm$CH₂$\frac{1}{3}$NH— | 114–119 |

EXAMPLE 12

Following the procedure described in Example 8 and using the compound from Example 1, the following compound of the formula

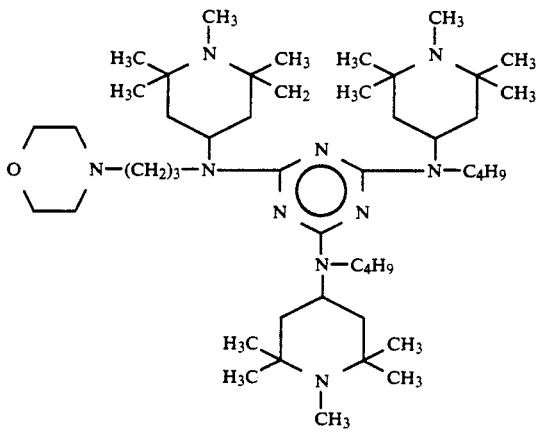

with a melting point of 87°–89° C. is prepared.

EXAMPLE 13

(Light-stabilizing action in polypropylene tapes): 1 g of each of the compounds indicated in Table 1, 1.0 g of tris-(2,4-di-t-butylphenyl) phosphite, 0.5 g of pentaerythritol tetrakis-[3-(3,5-di-t-butyl-4-hydroxyphenyl)-propionate] and 1 g of calcium stearate are mixed in a slow mixer with 1000 g of polypropylene powder of melt index=2 g/10 minutes (measured at 230° C. and 2.16 kg).

The mixtures are extruded at 200°–230° C. to give polymer granules which are then converted into stretched tapes of 50 μm thickness and 2.5 mm width, using a pilot-type apparatus (Leonard-Sumirago (VA) Italy) operating under the following conditions:

| Extruder temperature: | 210–230° C. |
|---|---|
| Head temperature: | 240–260° C. |
| Stretch ratio: | 1:6 |

The tapes thus prepared are exposed, mounted on a white card, in a model 65 WR Weather-O-Meter (ASTM D 2565-85) with a black panel temperature of 63° C. The residual tenacity is measured on samples taken after various times of exposure to light by means of a constant-speed tensometer; the exposure time (in hours) ($T_{50}$) needed to halve the initial tenacity is then calculated.

Tapes prepared under the same conditions as indicated above, but without addition of stabilizer, are exposed for comparison.

The results obtained are shown in Table 1.

TABLE 1

| Stabilizer | $T_{50}$ (hours) |
|---|---|
| none | 300 |
| Compound from Example 1 | 1500 |
| Compound from Example 4 | 1900 |
| Compound from Example 7 | 1650 |
| Compound from Example 9 | 1830 |
| Compound from Example 10 | 1500 |

EXAMPLE 14

(Light-stabilizing action in polypropylene fibres): 2.5 g of each of the products indicated in Table 2, 0.5 g of tris-(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°–230° C. to give polymer granules which are then converted into fibres, using a pilot-type apparatus (Leonard-Sumirago (VA)Italy) operating under the following conditions:

| Extruder temperature: | 200–230° C. |
|---|---|
| Head temperature: | 255–260° C. |
| Strech ratio: | 1:3.5 |
| Count: | 11 dtex per filament. |

The fibres thus prepared are exposed, mounted on a white card, in a model 65 WR Weather-O-meter (ASTM D 2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated.

Fibres prepared under the conditions indicated above, but without addition of the compounds of the invention, are exposed for comparison.

The results obtained are shown in Table 2.

TABLE 2

| Stabilizer | $T_{50}$ (hours) |
|---|---|
| none | 150 |
| Compound from Example 7 | 1050 |
| Compound from Example 9 | 1000 |
| Compound from Example 11 | 970 |

Example 15

(Antioxidant action in polypropylene plaques): 1 g of each of the compounds indicated in Table 3, 0.5 g of octadecyl 3-(3,5-di-t-butyl-4-hydroxyphenyl)-propionate, 1 g of tris-(2,4-di-t-butylphenyl)phosphite and 1 g of calcium stearate are mixed in a slow mixer with 1000 g of polypropylene powder of melt index=2 g/10 minutes (measured at 230° C. and 2.16 kg).

The mixtures are extruded twice at 200°-230° C. to give polymer granules which are then converted into plaques of 1 mm thickness by compression-moulding for 6 minutes at 230° C.

The plaques are then punched by means of a DIN 53 451 mould, and the specimens obtained are exposed in a forced-circulation air oven maintained at a temperature of 135° C.

The specimens are checked at intervals by folding them by 180°, in order to determine the time (in hours) needed to cause fracture.

Specimens prepared under the conditions indicated above, but without addition of the compounds of the present invention, are also exposed for comparison.

The results obtained are shown in Table 3.

TABLE 3

| Stabilizer | Time to fracture (in hours) |
|---|---|
| none | 550 |
| Compound from Example 1 | 1840 |
| Compound from Example 2 | 2400 |
| Compound from Example 3 | 1660 |
| Compound from Example 8 | 1950 |

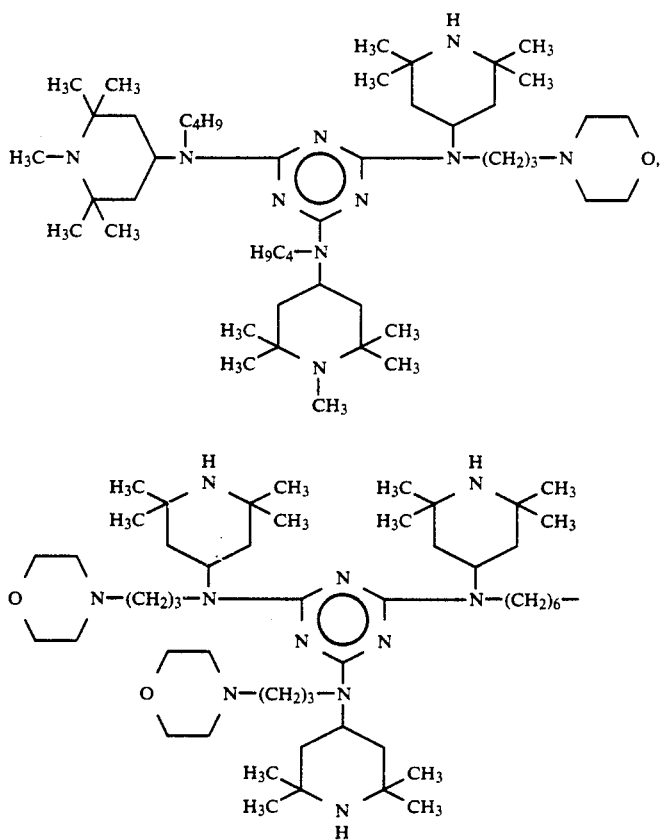

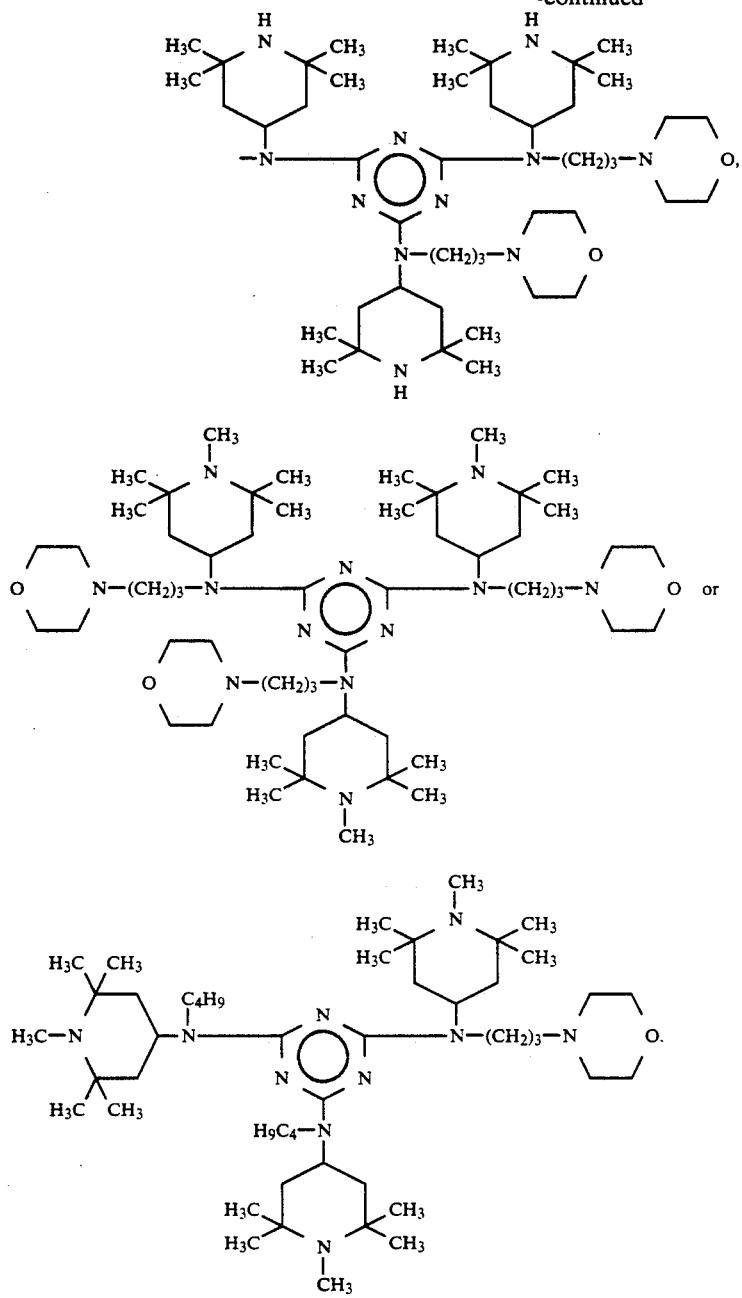

What is claimed is:

1. A compound of the formula (I)

$$\left( \begin{array}{c} R_1 \\ | \\ H_3C \diagdown \diagup N \diagdown \diagup CH_3 \\ H_3C \diagup \diagdown CH_3 \\ A-N-(CH_2)_{\overline{m}}-N \diagdown \diagup N \\ \diagdown N \diagup \\ | \\ R_2 \end{array} \right)_n - R_3$$

(I)

in which A is a direct bond, —O—, —CH$_2$— or —CH$_2$CH$_2$—, m is an integer from 2 to 6, R$_1$ is hydrogen, C$_1$-C$_8$alkyl, O, OH, NO, CH$_2$CN, C$_1$-C$_{18}$alkoxy, C$_5$-C$_{12}$cycloalkoxy, C$_3$-C$_6$alkenyl, C$_7$-C$_9$phenylalkyl unsubstituted or mono-, di- or tri-substituted on the phenyl by C$_1$-C$_4$alkyl; or C$_1$-C$_8$acyl, R$_2$ is a group —OR$_4$, —SR$_4$ or $$-\underset{\underset{R_5}{|}}{N}-R_6$$

where R$_4$, R$_5$ and R$_6$ which can be identical or different are hydrogen, C$_1$-C$_{18}$alkyl, C$_5$-C$_{12}$cycloalkyl unsubstituted or mono-, di- or tri-substituted by C$_1$-C$_4$alkyl; C$_3$-C$_{18}$alkenyl, phenyl which is unsubstituted or mono-, di- or tri-substituted by C$_1$-C$_4$alkyl or C$_1$-C$_4$alkoxy; C$_7$-C$_9$phenylalkyl unsubstituted or mono-, di- or tri-substituted on the phenyl by C$_1$-C$_4$alkyl; C$_2$-C$_4$alkyl which is substituted in the 2-, 3- or 4-position by C$_1$-C$_8$alkoxy or by di-(C$_1$-C$_4$alkyl)-amino; tetrahydrofurfuryl, a group of the formula (II)

$$A \diagup\!\!\!\diagdown N-(CH_2)_{\overline{m}}-$$

(II)

with A and m being as defined above, or a group of the formula (III)

$$R_7-N \diagup\!\!\!\diagdown \begin{array}{c} H_3C \; CH_3 \\ \\ H_3C \; CH_3 \end{array}$$

(III)

where R$_7$ is as defined for R$_1$, or $$-\underset{\underset{R_5}{|}}{N}-R_6$$

is a 1-pyrrolidyl, 1-piperidyl, 4-morpholinyl, 4-methyl-1-piperazinyl or 1-hexahydroazepinyl, or R$_2$ is any of the groups of the formulae (IVa)–(IVc)

$$R_7-N \diagup\!\!\!\diagdown \begin{array}{c} H_3C \; CH_3 \\ \\ H_3C \; CH_3 \end{array} \diagdown\!\!\!\diagup N \diagdown\!\!\!\diagup N-,$$

(IVa)

$$R_7-N \diagup\!\!\!\diagdown \begin{array}{c} H_3C \; CH_3 \\ \\ H_3C \; CH_3 \end{array} \diagdown\!\!\!\diagup N \diagdown\!\!\!\diagup N-(CH_2)_{2-3}-N- \begin{array}{c} H_3C \diagdown \diagup CH_3 \\ H_3C \diagup N \diagdown CH_3 \\ | \\ R_7 \end{array},$$

(IVb)

-continued

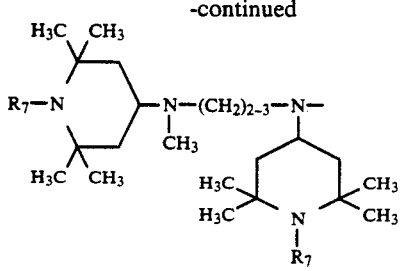  (IVc)

with $R_7$ as defined above, n is 1, 2, 3 or 4, and, if n is 1, $R_3$ is as defined for $R_2$, and, if n is 2, $R_3$ is one of the groups of the formulae (Va)-(Vc)

$$-E_1-R_8-E_2-, \qquad \text{(Va)}$$

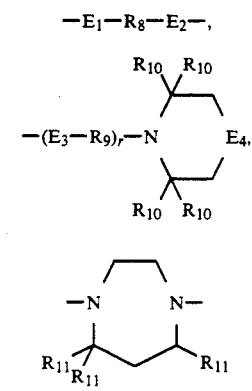  (Vb)

(Vc)

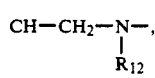

in which $E_1$, $E_2$ and $E_3$ which can be identical or different are $-O-$ or $>N-R_{12}$, $R_8$ is $C_2-C_{12}$alkylene, $C_4-C_{12}$alkylene interrupted by 1, 2 or 3 oxygen atoms or by 1 or $2>N-R_{12}$ groups; cyclohexylene, cyclohexylenedimethylene, methylenedicyclohexylene, isopropylidenedicyclohexylene, phenylene, isopropylidenediphenylene or xylylene, $R_9$ is $C_2-C_6$alkylene, $E_4$ is $>N-(R_9-E_3)_s-$, $>CHO-$ or $>$

r and s which can be identical or different are zero or 1, $R_{10}$ is hydrogen or, when r is 1 and $E_4$ is $>CHO-$, can also be methyl, $R_{11}$ is hydrogen or methyl and $R_{12}$ is hydrogen, $C_1-C_{18}$alkyl, $C_5-C_{12}$cycloalkyl unsubstituted or mono-, di- or tri-substituted by $C_1-C_4$alkyl; $C_7-C_9$phenylalkyl unsubstituted or mono-, di- or tri-substituted on the phenyl by $C_1-C_4$alkyl; or a group of the formula (III), and, if n is 3, $R_3$ is one of the groups of the formulae (VIa)-(VId)

$$-E_5-R_{13}-N-R_{14}-E_6-, \qquad \text{(VIa)}$$

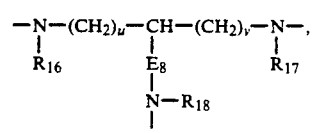

(VIb)

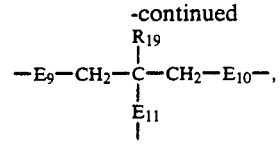  (VIc)

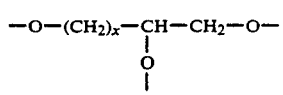  (VId)

in which $E_5$, $E_6$, $E_7$, $E_9$, $E_{10}$ and $E_{11}$ which can be identical or different are as defined above for $E_1$, $E_2$ and $E_3$; and, if $E_9$ and $E_{10}$ are both $-O-$, $E_{11}$ can also be a $-CH_2O-$ group, $R_{13}$, $R_{14}$ and $R_{15}$ which can be identical or different are $C_2-C_6$alkylene, t is zero or 1, $R_{16}$, $R_{17}$ and $R_{18}$ which can be identical or different are as defined above for $R_{12}$, $E_8$ is a direct bond or $-CH_2-$, u, v and x which can be identical or different are integers from 2 to 6 and $R_{19}$ is hydrogen or $C_1-C_8$alkyl, and, if n is 4, $R_3$ is a group of the formula (VIIa) or (VIIb)

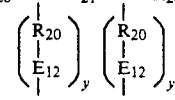  (VIIa)

  (VIIb)

in which $E_{12}$ is as defined above for $E_1$, $E_2$ and $E_3$; $R_{20}$ and $R_{21}$ which can be identical or different are $C_2-C_6$alkylene, y is zero or 1 and $R_{22}$ is $C_4-C_{12}$alkanetetrayl.

2. A compound of the formula (I) according to claim 1, in which $R_1$ and $R_7$ which can be identical or different are hydrogen, $C_1-C_4$alkyl, OH, $C_6-C_{12}$alkoxy, $C_5-C_8$cycloalkoxy, allyl, benzyl or acetyl.

3. A compound of the formula (I) according to claim 1, in which A is a direct bond, $-O-$ or $-CH_2-$, m is an integer from 2 to 4, $R_2$ is a group $-OR_4$, $-SR_4$ or $$-\underset{R_5}{\underset{|}{N}}-R_6$$

where $R_4$, $R_5$ and $R_6$ which can be identical or different are hydrogen, $C_1-C_{14}$alkyl, $C_5-C_8$cycloalkyl unsubstituted or mono-, di- or tri-substituted by $C_1-C_4$alkyl; $C_3-C_{12}$alkenyl, phenyl, benzyl, $C_2-C_3$alkyl which is substituted in the 2- or 3-position by $C_1-C_4$alkoxy or by di-($C_1-C_4$alkyl)-amino; tetrahydrofurfuryl, a group of the formula (II) or a group of the formula (III), or $$-\underset{R_5}{\underset{|}{N}}-R_6$$

is 1-pyrrolidyl, 1-piperidyl, 4-morpholinyl, 4-methyl-1-piperazinyl or 1-hexahydroazepinyl, or $R_2$ is one of the groups of the formulae (IVa)-(IVc), n is 1, 2, 3 or 4 and, if n is 1, $R_3$ is as defined for $R_2$, and, if n is 2, $R_3$ is one of the groups of the formulae (Va)-(Vc) in which $E_1$, $E_2$ and $E_3$ which can be identical or different are $-O-$ or $>N-R_{12}$, $R_8$ is $C_2-C_{10}$alkylene, $C_4-C_{10}$alkylene interrupted by 1, 2 or 3 oxygen atoms or 1 or $2>N-R_{12}$ groups; cyclohexylenedimethylene, methylenedicyclohexylene, isopropylidenedicyclohexylene, isopropylidenediphenylene or xylylene, $R_9$ is $C_2$-$C_4$alkylene, $E_4$ is $>$N—$(R_9$-$E_3)_s$—, $>$CHO— or $>$

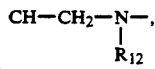

r and s which can be identical or different are zero or 1, $R_{10}$ is hydrogen or, when r is 1 and $E_4$ is $>$CHO—, can also be methyl, $R_{11}$ is hydrogen or methyl and $R_{12}$ is hydrogen, $C_1$-$C_{12}$alkyl, $C_5$-$C_8$cycloalkyl unsubstituted or mono-, di- or tri-substituted by $C_1$-$C_4$alkyl; benzyl or a group of the formula (III), and, if n is 3, $R_3$ is one of the groups of the formulae (VIa)-(VId) in which $E_5$, $E_6$, $E_7$, $E_9$, $E_{10}$ and $E_{11}$ which can be identical or different are as defined above for $E_1$, $E_2$ and $E_3$; and, if $E_9$ and $E_{10}$ are both —O—, $E_{11}$ can also be a —$CH_2O$— group, $R_{13}$, $R_{14}$ and $R_{15}$ which can be identical or different are $C_2$-$C_6$alkylene, t is zero or 1, $R_{16}$, $R_{17}$ and $R_{18}$ which can be identical or different are as defined above for $R_{12}$, $E_8$ is a direct bond or —$CH_2$—, u, v and x which can be identical or different are integers from 2 to 6 and $R_{19}$ is hydrogen or $C_1$-$C_4$alkyl, and, if n is 4, $R_3$ is a group of the formula (VIIa) or (VIIb) in which $E_{12}$ is as defined above for $E_1$, $E_2$ and $E_3$; $R_{20}$ and $R_{21}$ which can be identical or different are $C_2$-$C_6$alkylene, y is zero or 1 and $R_{22}$ is $C_4$-$C_8$alkanetetrayl.

4. A compound of the formula (I) according to claim 1, in which A is —O— or —$CH_2$—, m is 2 or 3, $R_2$ is a group —$OR_4$, —$SR_4$ or

where $R_4$, $R_5$ and $R_6$ which can be identical or different are hydrogen, $C_1$-$C_{12}$alkyl, cyclohexyl which is unsubstituted or mono-, di- or tri-substituted by $C_1$-$C_4$alkyl; allyl, undecenyl, phenyl, benzyl, $C_2$-$C_3$alkyl which is substituted in the 2- or 3-position by $C_1$-$C_4$alkoxy, by dimethylamino or by diethylamino; tetrahydrofurfuryl, a group of the formula (II) or a group of the formula (III), or

is 4-morpholinyl, or $R_2$ is one of the groups of the formulae (IVa)-(IVc), n is 1, 2, 3 or 4 and, if n is 1, $R_3$ is as defined above for $R_2$, and, if n is 2, $R_3$ is one of the groups of the formulae (Va)-(Vc) in which $E_1$, $E_2$ and $E_3$ which can be identical or different are —O— or $>$N-$R_{12}$, $R_8$ is $C_2$-$C_8$alkylene, $C_6$-$C_{10}$alkylene interrupted by 2 or 3 oxygen atoms, cyclohexylenedimethylene, methylenedicyclohexylene, isopropylidenedicyclohexylene, isopropylidenediphenylene or xylylene, $R_9$ is $C_2$-$C_3$alkylene, $E_4$ is $>$N—$(R_9$—$E_3)_s$— or $>$CHO—, r and s which can be identical or different are zero or 1, $R_{10}$ is hydrogen or, when r is 1 and $E_4$ is $>$CHO—, can also be methyl, $R_{11}$ is hydrogen or methyl and $R_{12}$ is hydrogen, $C_1$-$C_8$alkyl, cyclohexyl which is unsubstituted or mono-, di- or tri-substituted by $C_1$-$C_4$alkyl, benzyl or a group of the formula (III), and, if n is 3, $R_3$ is one of the groups of the formulae (VIa)-(VId) in which $E_5$, $E_6$, $E_7$, $E_9$, $E_{10}$ and $E_{11}$ which can be identical or different are as defined above for $E_1$, $E_2$ and $E_3$; and, if $E_9$ and $E_{10}$ are both —O—, $E_{11}$ can also be a —$CH_2O$— group, $R_{13}$, $R_{14}$ and $R_{15}$ which can be identical or different are $C_2$-$C_6$alkylene, t is zero or 1, $R_{16}$, $R_{17}$ and $R_{18}$ which can be identical or different are as defined above for $R_{12}$, $E_8$ is a direct bond or —$CH_2$—, u, v and x which can be identical or different are integers from 2 to 6 and $R_{19}$ is hydrogen, methyl or ethyl, and, if n is 4, $R_3$ is a group of the formula (VIIa) or (VIIb) in which $E_{12}$ is as defined above for $E_1$, $E_2$ and $E_3$; $R_{20}$ and $R_{21}$ which can be identical or different are $C_2$-$C_6$alkylene, y is zero or 1 and $R_{22}$ is $C_4$-$C_6$alkanetetrayl.

5. A compound of the formula (I) according to claim 1, in which A is —O—, m is 2 or 3, $R_2$ is a group —$OR_4$ or

where $R_4$ is $C_1$-$C_8$alkyl or a group of the formula (III) and $R_5$ and $R_6$, which can be identical or different are $C_1$-$C_8$alkyl, cyclohexyl, benzyl, $C_2$-$C_3$alkyl substituted in the 2- or 3-position by methoxy, by ethoxy, by dimethylamino or by diethylamino; tetrahydrofurfuryl, a group of the formula (II) or a group of the formula (III), or $R_5$ can also be hydrogen, or

is 4-morpholinyl, or $R_2$ is one of the groups of the formulae (IVa)-(IVc), n is 1, 2, 3 or 4 and, if n is 1, $R_3$ is as defined for $R_2$ and, if n is 2, $R_3$ is one of the groups of the formulae (Va)-(Vc) in which $E_1$ and $E_2$ which can be identical or different are —O— or $>$N-$R_{12}$, $R_8$ is $C_2$-$C_8$alkylene, $C_6$-$C_{10}$alkylene interrupted by 2 or 3 oxygen atoms, cyclohexylenedimethylene or methylenedicyclohexylene, the group (Vb) is

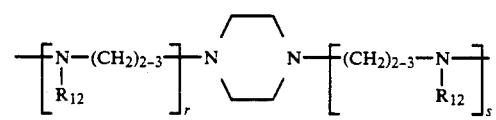

or

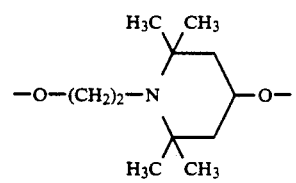

where r and s which can be identical or different are zero or 1, $R_{12}$ is hydrogen, $C_1$-$C_4$alkyl, cyclohexyl or a group of the formula (III) and $R_{11}$ is hydrogen or methyl, and, if n is 3, $R_3$ is a group of the formula (VIa) or (VIb) in which $E_5$, $E_6$ and $E_7$ which can be identical or different are as defined above for $E_1$ and $E_2$; $R_{13}$, $R_{14}$ and $R_{15}$ which can be identical or different are $C_2$-$C_6$alkylene, t is zero or 1, $R_{16}$, $R_{17}$ and $R_{18}$ which can be identical or different are as defined above for $R_{12}$; $E_8$ is a direct bond or —$CH_2$— and u and v which can be identical or different are integers from 3 to 6, and, if n is 4, $R_3$ is a group of the formula (VIIa) in which $E_{12}$ is as defined above for $E_1$ and $E_2$; $R_{20}$ and $R_{21}$ which can be identical or different are $C_2$-$C_3$alkylene and y is zero or 1.

6. A compound of the formula (I) according to claim 1, in which $R_1$ is hydrogen or methyl, A is —O—, m is 3, $R_2$ is a group —$OR_4$ or

$R_4$ is $C_1$-$C_4$alkyl, 2,2,6,6-tetramethyl-4-piperidyl or 1,2,2,6,6-pentamethyl-4-piperidyl, $R_5$ and $R_6$ which can be identical or different are $C_1$-$C_8$alkyl, cyclohexyl, tetrahydrofurfuryl, a group

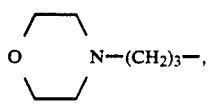

2,2,6,6-tetramethyl-4-piperidyl or 1,2,2,6,6-pentamethyl-4-piperidyl, or $R_5$ can also be hydrogen, or

is 4-morpholinyl, n is 1, 2, 3 or 4 and, if n is 1, $R_3$ is as defined above for $R_2$ and, if n is 2, $R_3$ is a group of the formula (Va) in which $E_1$ and $E_2$ which can be identical or different are >N-$R_{12}$, $R_8$ is $C_2$-$C_6$alkylene, $C_8$-$C_{10}$alkylene interrupted by 2 or 3 oxygen atoms or methylenedicyclohexylene and $R_{12}$ is hydrogen, methyl, 2,2,6,6-tetramethyl-4-piperidyl or 1,2,2,6,6-pentamethyl-4-piperidyl, and, if n is 3, $R_3$ is a group

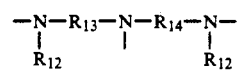

in which $R_{12}$ is as defined above and $R_{13}$ and $R_{14}$ which can be identical or different are $C_2$-$C_3$alkylene, and, if n is 4, $R_3$ is a group

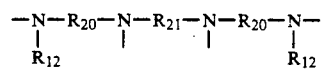

in which $R_{12}$ is as defined above and $R_{20}$ and $R_{21}$ which can be identical or different are $C_2$-$C_3$alkylene.

7. A compound of the formula (I) according to claim 1, which is